United States Patent
Rossel

(10) Patent No.: US 11,147,774 B2
(45) Date of Patent: Oct. 19, 2021

(54) PEELABLE NAIL LACQUER

(71) Applicant: OYSTERSHELL NV, Merelbeke (BE)

(72) Inventor: Bart Rossel, Nederzwalm (BE)

(73) Assignee: OYSTERSHELL NV, Merelbeke (BE)

( * ) Notice: Subject to any disclaimer, the term of this patent is extended or adjusted under 35 U.S.C. 154(b) by 0 days.

(21) Appl. No.: 16/488,454

(22) PCT Filed: Feb. 23, 2018

(86) PCT No.: PCT/EP2018/054597
§ 371 (c)(1),
(2) Date: Aug. 23, 2019

(87) PCT Pub. No.: WO2018/154085
PCT Pub. Date: Aug. 30, 2018

(65) Prior Publication Data
US 2020/0030249 A1 Jan. 30, 2020

(30) Foreign Application Priority Data

Feb. 24, 2017 (BE) .................................. 2017/5115
Sep. 27, 2017 (EP) .................................. 17193522

(51) Int. Cl.
| | | |
|---|---|---|
| A61K 9/70 | (2006.01) | |
| A61K 8/04 | (2006.01) | |
| A61K 8/87 | (2006.01) | |
| A61K 9/10 | (2006.01) | |
| A61K 45/00 | (2006.01) | |
| A61K 47/02 | (2006.01) | |
| A61K 47/12 | (2006.01) | |
| A61Q 3/02 | (2006.01) | |
| A61P 31/10 | (2006.01) | |
| A46B 9/02 | (2006.01) | |
| A61K 31/19 | (2006.01) | |
| A61K 47/34 | (2017.01) | |
| A45D 34/04 | (2006.01) | |

(52) U.S. Cl.
CPC .......... *A61K 9/7015* (2013.01); *A45D 34/045* (2013.01); *A46B 9/021* (2013.01); *A61K 8/044* (2013.01); *A61K 8/87* (2013.01); *A61K 9/10* (2013.01); *A61K 9/7007* (2013.01); *A61K 31/19* (2013.01); *A61K 45/00* (2013.01); *A61K 47/02* (2013.01); *A61K 47/12* (2013.01); *A61K 47/34* (2013.01); *A61P 31/10* (2018.01); *A61Q 3/02* (2013.01); *A46B 2200/1046* (2013.01)

(58) Field of Classification Search
None
See application file for complete search history.

(56) References Cited

U.S. PATENT DOCUMENTS

| | | | | |
|---|---|---|---|---|
| 2,904,808 | A * | 9/1959 | Massman | A45D 34/048 |
| | | | | 401/4 |
| 5,830,443 | A | 11/1998 | Lee | |
| 6,238,679 | B1 | 5/2001 | De La Poterie | |
| 7,700,082 | B2 * | 4/2010 | Mallo | C08G 18/4277 |
| | | | | 424/70.11 |
| 2003/0007944 | A1 | 1/2003 | O'Halloran et al. | |
| 2008/0112908 | A1 * | 5/2008 | Srulevitch | A61K 31/185 |
| | | | | 424/61 |
| 2016/0095811 | A1 | 4/2016 | Swick et al. | |
| 2017/0216190 | A1 * | 8/2017 | Viala | A61K 8/41 |

FOREIGN PATENT DOCUMENTS

| | | |
|---|---|---|
| GB | 2478159 A | 8/2011 |
| WO | 2016/193626 A1 | 12/2016 |

OTHER PUBLICATIONS

Dictionary.com definition for "providing"; accessed Jun. 29, 2020 (Year: 2020).*
Medicament definition, Dictionary.com, accessed Dec. 30, 2020 (Year: 2020).*
International Preliminary Report on Patentability for Application No. PCT/EP2018/054597, dated May 27, 2019 in 12 pages.
Belgium Search Report for Application No. BE201705115, dated Oct. 26, 2017 in 13 pages.

* cited by examiner

*Primary Examiner* — Melissa S Mercier
(74) *Attorney, Agent, or Firm* — Knobbe, Martens, Olson & Bear, LLP

(57) ABSTRACT

The present invention provides a liquid composition comprising a pharmaceutically active compound and an aqueous polymer dispersion, wherein said liquid composition forms a film upon drying under standard ambient temperature and pressure; a method for providing the same; and a container comprising said liquid composition.

13 Claims, No Drawings

PEELABLE NAIL LACQUER

CROSS-REFERENCE TO RELATED APPLICATIONS

This application is the U.S. National Phase under 35. U.S.C. § 371 of International Application PCT/EP2018/054597, filed Feb. 23, 2018, which claims priority to Belgium Patent Application No. 2017/5115 and European Patent Application No. 17193522.4, filed Sep. 27, 2017. The disclosures of the above-described applications are hereby incorporated by reference in their entirety.

TECHNICAL FIELD

The present invention relates to the field of pharmaceutical lacquers, more specifically pharmaceutical nail lacquers.

INTRODUCTION

Dermal transmission of a pharmaceutical agent is known in the form of viscous compositions or films from which the pharmaceutical agent is released into the subject. Recent developments have focussed on compositions that can easily be applied by patients themselves.

WO 2013/188222 from Atrium Medical Corporation discloses gels and coating biomaterials which are covered by a fixating film for controlling drug delivery to a body part. Such systems do not allow for accurate, site-specific dosing of the drug delivering composition.

A series of patent applications describe curable pre-polymer compositions. WO 99/17814 describes in situ film forming polymer films to be applied on the skin surface to cover a wound and to be polymerized thereafter, thereby forming an antimicrobial biocompatible polymeric film. The compositions are not polyurethane based but define vinyl-polymerizable monomers, the composition thereby needing also a polymerization initiator. Such systems clearly have the disadvantage of a difficult to control polymerization process and possible contamination of wounds by initiator or plasticizers. U.S. Pat. No. 7,906,134 and U.S. Pat. No. 8,475,822 disclose similar, room temperature curable compositions.

EP 943 310 by L'Oréal discloses a film forming composition comprising a polymer dispersion, with an average particle diameter of the polymer dispersion of 2 to 100 nm. The examples therein show compositions of up to about 35 wt. % of the commercially available polyester-polyurethane dispersion Avalure® UR-405, and need to be scrubbed-off after use, often requiring organic solvents such as acetone, ethyl lactate, etc. to allow for efficient removal.

The present invention seeks to provide a nail lacquer composition for treating a fungal nail infection, which nail lacquer composition (i) can easily be applied by the patients themselves, (ii) can be worn for at least one day—thereby allowing for a less frequent application regimen, and (iii) can be peeled off as one layer after use. This requires that the nail lacquer is provided as a viscous liquid or paste which can be distributed within the contours of the infected nail. Furthermore, the applied layer must be water and stress resistant to ensure an application time of about 24 hours.

SUMMARY OF THE INVENTION

The current invention provides in a solution for at least one of the above mentioned problems by providing a peelable nail lacquer.

In a first aspect, the present invention provides a liquid composition comprising a pharmaceutically active compound and an aqueous polymer dispersion, wherein said liquid composition forms a film upon drying under standard ambient temperature and pressure.

This is advantageous because said liquid composition (i) can easily be applied by the patients themselves, (ii) can be worn for at least one day - thereby allowing for a less frequent application regimen, i.e. once per day, and (iii) can be peeled off as one layer after use.

In a second aspect, the present invention provides a liquid composition according to the first aspect of the invention for use as a medicament.

In a third aspect, the present invention provides a liquid composition according to the first aspect of the invention for use in treatment of nail diseases.

In a fourth aspect, the present invention provides a method for providing a liquid composition according to the first aspect of the invention, comprising the steps of mixing at least a pharmaceutically active compound and an aqueous polymer dispersion.

In a fifth aspect, the present invention provides a container comprising a liquid composition according to the first aspect of the invention.

DETAILED DESCRIPTION OF THE INVENTION

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints. All percentages are to be understood as percentage by weight and are abbreviated as "wt. %", unless otherwise defined or unless a different meaning is obvious to the person skilled in the art from its use and in the context wherein it is used.

The phrase "pharmaceutically active agent" is employed herein to refer to those compounds, materials, compositions, and/or dosage forms which are, within the scope of sound medical judgment, suitable for use in contact with the tissues of human beings and/or animals without excessive toxicity, irritation, allergic response, or other problem or complication, commensurate with a reasonable benefit/risk ratio, and which have an therapeutic or prophylactic effect on a disease or infection of tissues of said human beings and/or animals when applied in an effective amount. By the term "effective amount" is meant the amount or quantity of the elemental additive salt that is sufficient to elicit the required or desired response, or in other words, the amount that is sufficient to elicit an appreciable biological response when administered to a subject. As used herein, the term "patient" or "subject" are taken to mean warm blooded animals such as mammals, for example, horses, cows, sheep and humans.

In a first aspect, the present invention provides a liquid composition comprising a pharmaceutically active compound and an aqueous polymer dispersion, wherein said liquid composition forms a film upon drying under standard ambient temperature and pressure.

This is advantageous because said liquid composition (i) can easily be applied by the patients themselves, (ii) can be worn for at least one day—thereby allowing for a less frequent application regimen, i.e. once per day, and (iii) can be peeled off as one layer after use. Nail lacquers according to the invention are provided as a viscous liquid or paste which can be distributed within the contours of the infected nail or even to surrounding tissue. Furthermore, the applied layer is water and stress resistant to ensure an application time of at least about 24 hours.

Preferably, said polymer is a thermoplastic polymer. Preferably, said liquid composition has a viscosity of higher than 250 mPa·s, higher than 500 mPa·s, or even higher than 1000 mPa·s, upon drying for 180 sec under standard ambient temperature and pressure. Accordingly, the formed film is 'dry-to-touch.'

In a preferred embodiment, the present invention provides a liquid composition according to the first aspect of the invention, wherein said aqueous polymer dispersion comprises a polymer content of at least 25 wt. % relative to the total weight of the composition, as determined according to DIN EN ISO 3251. Preferably, said liquid composition has a polymer content of at least 27 wt. %, 30 wt. %, 32 wt. % or 35 wt. % and more preferably of 36 wt. %, 37 wt. %, 38 wt. %, 39 wt. %, 40 wt. %, 41 wt. %, 42 wt. %, 43 wt. %, 44 wt. % or 45 wt. %, or any amount there in between. A higher polymer content allows for proper solidifying characteristics. Preferably, said polymer content is lower than 50 wt. %. When polymer content is too high, the liquid composition is too viscous and renders application to a tissue difficult.

In a preferred embodiment, the present invention provides a liquid nail lacquer composition according to the first aspect of the invention, wherein said liquid nail lacquer composition is free of any cosmetically acceptable thickening agents, such as i.e. aluminium silicate, calcium silicate, magnesium aluminium silicate, magnesium silicate, magnesium trisilicate, sodium magnesium silicate, zirconium silicate, Attapulgite, Bentonite, Fuller's Earth, Hectorite, kaolin, lithium magnesium silicate, lithium magnesium sodium silicate, Montmorillonite, Pyrophyllite and Zeolite. Preferably, said liquid nail lacquer composition is free of any cosmetically acceptable thickening agents selected of the group consisting of magnesium aluminum silicate, magnesium silicate, magnesium trisilicate, Attapulgite, Bentonite, Hectorite, lithium magnesium silicate, lithium magnesium sodium silicate, Montmorillonite. This is advantageous since thickening agents such as magnesium aluminium silicate are difficult in processing during the preparation of the liquid nail lacquer composition, compared to regular liquids or solutes.

In a preferred embodiment, the present invention provides a liquid nail lacquer composition according to the first aspect of the invention, wherein said liquid nail lacquer composition is free of any cosmetically acceptable particulates, such as i.e. silica particulates. This is advantageous since particulates may be difficult in processing during the preparation of the liquid nail lacquer composition, compared to regular liquids or solutes.

In a preferred embodiment, the present invention provides a liquid nail lacquer composition according to the first aspect of the invention, wherein said liquid nail lacquer composition essentially consists of an organic acid and an aqueous polymer dispersion comprising a film forming polymer, whereby said film forming polymer is comprised in said liquid nail lacquer composition in an amount of at least 25 wt. %, relative to the total weight of the composition, as determined according to DIN EN ISO 3251. Preferably, said film forming polymer is comprised in said liquid nail lacquer composition in an amount of polymer content of at least 30 wt. %, relative to the total weight of the composition, more preferably at least 35 wt. % and even more preferably at least 37 wt. % or even 38 wt. %.

In a preferred embodiment, the present invention provides a liquid nail lacquer composition according to the first aspect of the invention, wherein said liquid nail lacquer composition comprises at most 10 wt. % of hydrophobic solvents, relative to the total weight of the nail lacquer composition, preferably at most 8 wt. % of hydrophobic solvents, more preferably at most 5 wt. % of hydrophobic solvents.

The liquid nail lacquer composition comprises water as solvent and may further comprise at least one non-toxic hydrophilic solvent selected of the group consisting of ethanol, n-propanol, i-propanol, ethylene glycol, 1,2- and 1,3-propylene glycol and glycerol, preferably ethylene glycol, 1,2-propylene glycol and glycerol. Said non-toxic hydrophilic solvent is a volatile organic solvent having a boiling point lower than 135° C., lower than 120° C., lower than 100° C., preferably lower than 90° C., more preferably lower than 80° C. Preferably, said non-toxic hydrophilic solvent is comprised in an amount of less than 15 wt. %, relative to the total weight of the nail lacquer composition, preferably in an amount of less than 10 wt. %, more preferably in an amount of less than 8 wt. % or even less than 5 wt. %. This is advantageous to allow for fast drying times, thereby ensure ease of application by the user, eventually resulting in higher compliance and thus better curing rates. In an alternative, and preferred embodiment, no hydrophilic solvent is comprised.

In a preferred embodiment, the present invention provides a liquid composition according to the first aspect of the invention, wherein said polymer has a glass transition temperature lower than −30° C., as determined according to DIN EN ISO 61 006. In a more preferred embodiment, said polymer has a glass transition temperature lower than −35° C. and higher than −95° C. Preferably, said polymer has a glass transition temperature lower than −40° C. and higher than −100° C., and more preferably between −40° C. and −90° C. Most preferably, said polymer has a glass transition temperature of −85° C., −80° C., −75° C., −70° C., −65° C., −60° C., −55° C., −50° C., −45° C. or −40° C. or any value there in between. This is advantageous to provide for a sufficiently flexible and soft film which is formed upon drying of the liquid composition. A lower Tg enhances proper film forming.

In a preferred embodiment, the present invention provides a liquid composition according to the first aspect of the invention, comprising water in an amount of at most 60 wt. %. Preferably, said liquid composition has a water content of at least 35 wt. % and at most 55 wt. %, and more preferably of 44 wt. %, 46 wt. %, 48 wt. %, 50 wt. %, 52 wt. % or 54 wt. %, or any amount there in between. An optimized water content can be found in order to optimize the viscosity of the liquid composition to allow for ease of application to a tissue to be treated.

In a preferred embodiment, the present invention provides a liquid composition according to the first aspect of the invention, comprising volatile organic compounds in an amount of less than 15 wt. %, relative to the total weight of the composition. More preferably, said composition comprising volatile organic compounds in an amount of less than 5 wt. %, and even more preferably in an amount of less than 2.5 wt. %. Most preferably, said liquid composition does not comprise any volatile organic compounds. The term "volatile organic compounds" is to be understood as an organic compound having a boiling point lower than 100° C., and more preferably lower than 80° C., or even lower than 70° C. or lower than 60° C.

In a preferred embodiment, the present invention provides a liquid composition according to the first aspect of the invention, having a pH of between 2.5 and 6.5, as determined according to DIN ISO 976. Preferably, said liquid composition has a pH between 3.0 and 5.5 and more preferably, said liquid composition has a pH equal to 3.0, 3.5, 4.0, 4.5, or any value there in between. An acidic composition contributes to nail disease treatment.

In a preferred embodiment, the present invention provides a liquid composition according to the first aspect of the invention, having a minimal film forming temperature of at most 5° C., as determined according to DIN EN ISO 2115. Preferably, said liquid composition has a minimal film forming temperature of at most 0° C. This ensures that the liquid composition upon application to a subject's tissue properly forms a film within a convenient time limit.

In a preferred embodiment, the present invention provides a liquid composition according to the first aspect of the invention, wherein said liquid composition has a viscosity of at most 500,000 mPa·s, as determined according to DIN EN ISO 3219. Preferably, said liquid nail lacquer composition has a viscosity of between 250 mPa·s and 100,000 mPa·s, and more preferably between 500 mPa·s and 75,000 mPa·s. Even more preferably, said liquid nail lacquer composition has a viscosity of between 1,000 mPa·s and 50,000 mPa·s, such as i.e. 2,000 mPa·s, 5,000 mPa·s, 10,000 mPa·s, 20,000 mPa·s, 30,000 mPa·s or 40,000 mPa·s, or any value there in between. An optimized viscosity allows for proper application of the liquid composition to a subject's tissue.

In a preferred embodiment, the present invention provides a liquid composition according to the first aspect of the invention, wherein said polymer dispersion has an average particle size d(0.5) between 50 nm and 50 μm, as determined by laser diffraction, more specifically as determined by Coulter laser diffraction.

Preferably, said polymer dispersion has an average particle size between 75 nm and 5 μm, and more preferably between 100 nm and 1000 nm, and most preferably of about 100 nm, 125 nm, 150 nm, 175 nm, 200 nm, 225 nm, 250 nm, 275 nm, 300 nm, 325 nm, 350 nm or 375 nm, or any value there in between. Such polymer dispersion provides for sufficiently fast drying coatings and good film forming characteristics by fusing upon drying.

In a preferred embodiment, the present invention provides a liquid composition according to the first aspect of the invention, wherein said film has an elongation at break of at least 100%, as determined according to DIN EN ISO 527-3:2003-07, more specifically DIN EN ISO 527-3:2003-07 "Plastics; Determination of tensile properties; Part 3: test conditions for films and sheets."

More preferably, said film has an elongation at break of at least 250%, at least 500%, at least 750%, and even more preferably at least 1000%. A sufficiently high elongation at break ensures that the film can easily be removed as one layer without breaking, thus providing excellent peel-off characteristics. Most preferably, said film has an elongation at break of about 1200%, 1400%, 1600%, 1800%, 2000%, 2200%, 2400%, 2600% or 2800%, or any value there in between. Also, said film has preferably an elongation at break of at most 5000%, 4000% or most preferably at most 3000%.

In a preferred embodiment, the present invention provides a liquid composition according to the first aspect of the invention, wherein said film has a tensile strength at break of at least 5 MPa, as determined according to DIN EN ISO 527-3:2003-07, more specifically DIN EN ISO 527-3:2003-07 "Plastics; Determination of tensile properties; Part 3: test conditions for films and sheets."

More preferably, said film has a tensile strength at break of at least 10 MPa, at least 12 MPa, at least 14 MPa or at least 16 MPa. More preferably, said film has a tensile strength at break of 16 MPa, 18 MPa, 20 MPa, 22 MPa, 24 MPa, 26 MPa, 28 MPa or 30 MPa, or any value there in between. A sufficiently high tensile strength at break ensures that the film can easily be removed as one layer without breaking, thus providing excellent peel-off characteristics.

In a preferred embodiment, the present invention provides a liquid composition according to the first aspect of the invention, wherein said polymer is a film forming polymer selected from the group epoxy polymers, alkyd polymers, acrylic polymers, polyesters and polyurethanes, copolymers and/or blends thereof.

In a preferred embodiment, the present invention provides a liquid composition according to the first aspect of the invention, wherein said polymer is a poly(urea-urethane) polymer. The term "poly(urea-urethane) polymer" is meant to refer to (i) poly(urea) polymers comprising urea (-NRC(=O)NR'-) linkages, (ii) poly(urethane) polymers comprising urethane (-NRC(=O)OR'-) linkages, and (iii) polymers that include both urea (-NRC(=O)NR'-) and urethane (-NRC(=O)OR'-) linkages; wherein R and R' are each independently hydrogen, alkyl, as defined herein, or aryl, as defined herein. Preferably, said poly(urea-urethane) polymer comprises both urea and urethane linkages. All polymers herein are described according to the monomer units that react to form the polymer, such as, e.g., polyamines, polyols, polyisocyanates, and the like. The term "polymer" will be understood to include polymers, copolymers (e.g., polymers formed using two or more different monomers), oligomers and combinations thereof, as well as polymers, oligomers, or copolymers that can be formed in a miscible blend.

The term "alkyl" refers to a straight, branched or cyclic hydrocarbon. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. Preferably, the term "alkyl" refers to a "lower alkyl."

The term "lower alkyl" is a subset of alkyl and refers to a hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" is intended to include both substituted and unsubstituted alkyl unless otherwise indicated. Substituted alkyl may be substituted with one or more (e.g., one, two or three) suitable functional groups including, e.g., halo, alkyl, alkoxy, haloalkyl, amino, hydroxyl, aryl, isocyanate, and the like.

The term "alkoxy" refers to the functional group -OR, wherein R is an alkyl, as defined herein.

The terms "aryl" and "arylene" refer to a monovalent or divalent, respectively, monocyclic carbocyclic ring system or a bicyclic carbocyclic fused ring system having one or more aromatic rings. Representative examples of aryl(ene) include, azulenyl(ene), indanyl(ene), indenyl(ene), naphthyl (idene), phenyl(ene), tetrahydronaphthyl(idene), and the like. The term "aryl(ene)" is intended to include both substituted and unsubstituted aryl unless otherwise indicated. Substituted aryl(ene) may be substituted with one or more suitable functional groups (e.g., one, two or three), including, e.g., alkyl and those groups set forth in connection with alkyl above.

The term "polyamine" is meant to refer to compounds having at least two (primary and/or secondary) amine functional groups per molecule. In preferred embodiments of the present invention, the poly(urea-urethane) polymer includes an aliphatic primary and/or secondary polyamine. The primary and/or secondary polyamine may also include various other functional groups within the polyamine, including polyether, polyester, polycarbonate and/or polypropylene linkages.

The term "polyol" is meant to refer to compounds having at least two hydroxyl functional groups per molecule. Some suitable polyols include, for example, polyglycols of the formula H(OCH$_2$CH$_2$)$_p$-OH, wherein p is an integer equal to 1 to 14, as for example when p is equal to 1 to 3, such compounds as ethylene glycol, propylene glycol, butylene glycols, such as 1,3-, 1,4-, and 2,3-butylene glycol, alkylene glycols having 5 to 9 carbon atoms; and polyglycols of an average molecular weight of about 600, such as polyethylene glycol 200, polyethylene glycol 400 and polyethylene glycol 600. The term "polyol" is to be understood as including one or more polyols, e.g., ethylene glycol and propylene glycol.

The term "polyisocyanate" and "polyisothiocyanate," collectively referred to as "polyiso(thio)cyanate" are meant to refer to compounds having at least two isocyanate or isothiocyanate, respectively, functional groups per molecule. Examples of monomeric polyisocyanates useful herein include polyisocyanates and polyisothiocyanates. Said polyisocyanate may be a carbo- or heterocyclic aromatic polyisocyanate such as, but not limited to, toluene diisocyanate (TDI), triphenylmethane-4,4',4"-triisocyanate, benzene-1,3,5-triisocyanate, toluene-2,4,6-triisocyanate, diphenyl-2,4,4'-triisocyanate, xylylene diisocyanate, chlorophenylene diisocyanate, diphenylmethane-4,4'-diisocyanate, naphthalene-1,5-diisocyanate, xylene-α,α'-diisothiocyanate, 3,3'-dimethyl-4,4'-biphenylene diisocyanate, 3,3'-dimethoxy-4,4'-biphenylene diisocyanate, 2,3,3'-dimethyl-4,4'-biphenylene diisocyanate, 5,5'-tetramethyl-4,4'-biphenylene diisocyanate, 2,2',5,5'-tetramethyl-4,4'-biphenylene diisocyanate, 4,4'-methylene bis (phenylisocyanate), 4,4'-sulfonylbis(phenylisocyanate), and the like. Preferably, said polyisocyanate is a cyclic or acyclic aliphatic polyisocyanate such as, but not limited to, ethylene diisocyanate, trimethylene diisocyanate, tetramethylene diisocyanate, pentamethylene diisocyanate, hexamethylene diisocyanate, cyclopentylene-1,3-diisocyanate, cyclohexylene-1,2-diisocyanate, cyclohexylene-1,4-diisocyanate, isophorone diisocyanate, ethylene diisocyanate, ethylene diisothiocyanate, and the like. Mixtures of any one or more of the above mentioned organic isothiocyanates or isocyanates may be used as desired.

In a preferred embodiment, the present invention provides a liquid composition according to the first aspect of the invention, wherein said poly(urea-urethane) polymer is comprised in an amount of at least 15 wt. % relative to the total weight of said composition, as determined according to DIN EN ISO 3251, and preferably in an amount of at least to 20 wt. %. More preferably, said poly(urea-urethane) polymer is comprised in an amount of at least 25 wt. % and most preferably in an amount of between 27 wt. % and 55 wt. %, and especially in an amount between 30 wt. % and 50 wt. %. Preferably, said liquid composition has a poly (urea-urethane) polymer content of at least 35 wt. % and more preferably of about 36 wt. %, 37 wt. %, 38 wt. %, 39 wt. %, 40 wt. %, 41 wt. %, 42 wt. %, 43 wt. %, 44 wt. % or 45 wt. %, or any amount there in between. A higher polymer content allows for proper solidifying characteristics. Preferably, said poly(urea-urethane) polymer content is lower than 50 wt. %.

In a preferred embodiment, the present invention provides a liquid composition according to the first aspect of the invention, wherein said aqueous polymer dispersion is an aqueous poly (urea-urethane) polymer dispersion. Preferably, said poly (urea-urethane) polymer is a polyether polyurethane polymer. Such polymers show an improved stability towards the organic acid in the composition. More preferably, said poly (urea-urethane) polymer is an aliphatic poly (urea-urethane) polymer, such as those prepared from aliphatic diols, aliphatic diamines and/or aliphatic diisocyanates. Even more preferably, said aliphatic poly (urea-urethane) polymer is a poly (urea-urethane) polymer prepared from 1,4-butanediol, ethylenediamine, hexamethylene diisocyanate and isophorone diisocyanate. This is advantageous since poly (urea-urethane) polymer, and especially aliphatic poly (urea-urethane) polymers exhibit less cracking under stress and is less brittle compared to i.e. acrylate polymers or copolymers. These aqueous poly (urea-urethane) polymer dispersions provide excellent film forming properties. They are preferably a colloidal system of a high molecular weight poly (urea-urethane) polymer dispersed in water.

In a preferred embodiment, an ionic monomer is incorporated into the polymer of aqueous dispersion to provide for an internal emulsifier. I.e., sodium N-(2-aminoethyl)-3-aminoethane sulfonate monomer can be incorporated in the poly (urea-urethane) polymer. An internal emulsifier is preferably incorporated into the polymer backbone to ensure stability of the dispersion. Therefore, the use of external surfactants is not required. As such, no contamination of tissues of the subject can take place. It leaves the skin cleaned, moisturized and smooth, without causing redness. Also, this allows to ensure sufficient stability of the polymer dispersion. More importantly, this offers the desired properties like highly flexible, clear, odourless and elastic film with good water resistance and adhesion to the tissue of the subject, i.e. nail tissue, enhances skin feeling, eliminates the need for alcohol and provides excellent aesthetics.

Furthermore, the preferred poly (urea-urethane) polymers exhibits good compatibility with a broad range of cosmetic ingredients including common synthetic and natural thickeners like i.e. xanthan gum, and polar solvents like i.e. ethanol, propanol and propylene glycol.

In a preferred embodiment, the present invention provides a liquid composition according to the first aspect of the invention, wherein said pharmaceutically active compound is an antimycotic agent. This is advantageous for the treatment of nail diseases or conditions. In one embodiment, the liquid composition of the invention comprises one or more active ingredients selected from the group consisting of synthetic or natural antifungal agents, antibiotics, antimicrobials, corticosteroids and nourishing and anabolic substances. In another embodiment, the liquid composition of the invention comprises one or more antifungal active ingredients selected from the group consisting of: (±)-cis-2,6-dimethyl-4-[2-methyl-3-(p-tert-pentyl-phenyl)propyl] morpholine (Amorolfin), amphotericin, 6-cyclohexyl-1-hydroxy-4-methyl-2(1H)-pyridone (Ciclopirox), bis-phenyl-(2-chlorophenyl)-1-imidazolylmethane (Clotrimazol), 1-[2-(2,4-dichlorophenyl)-2-(4-chlorobenzyloxy)-ethyl] imidazole (Econazol), 2,4-difluoro-α,α-bis(1H-1,2,4-triazole-1-ylmethyl)benzyl alcohol (Fluconazol), 5-fluorocytosine (Flucytosin), 7-Chloro-trimethoxy-methyl-spiro-[benzofuran-cyclohexene]-dione (Griseofulvin), 1-[2,4-dichloro-β-(2,6-dichlorobenzyloxy)-phenethyl]-imidazole (Isoconazol), (±)-1-sec-butyl-4-{4-[4-(4-{[(2R*,4S*)-2-(2,4-dichlorophenyl)-2-(1, 2,4-triazol-1-ylmethyl) -1,3-dioxolan-4-yl]methoxy}phenyl)-1-piperazinyl]phenyl}-4,5-dihydro-1,2,4-triazol-5-one (Itraconazol), (±) cis-1-acetyl-4-{4-([2-(2,4-dichlorophenyl)-2-(1H-imidazol-1-ylmethyl) -1,3-dioxolan-4-yl]methoxy)phenyl}piperazine (Ketoconazol), 1-[2,4-dichloro-β-(2,4-dichlorobenzyloxy)-phenyl-ethyl]imidazole (Miconazol), (E)-N-cinnamyl-N-methyl-l-naphthylmethylamine (Naftifin), Nystatin, (E)-(6,6-dimethyl-2-hepten-4-ynyl)-N-methyl-1-naphthylmethylamine (Terbinafin), 1-[2-{(2-chloro-3-thienyl)methoxy}-2-(2,4-dichloropheny)ethyl]-1H-imidazole (Tioconazol), O-2-naphthyl-N-methyl-N-(3-tolyl)-thiocarbamate (Tolnaftat), α-(2,4-difluorophenyl)-5-fluoro-β-methyl-α-(1H-1,2,4-triazol-1-ylmethyl)-4-pyrimidine ethanol (Voriconazol). In one embodiment, the liquid composition of the invention comprises one or more of anti-bacterial or anti-fungal active ingredients selected from the group consisting of tea tree essential oil, lavender oil, thuja oil, azadirachta indica extract and Australian Blue Cypress oil.

In a preferred embodiment, the present invention provides a liquid composition according to the first aspect of the invention, wherein said antimycotic agent is an organic acid, alkali salts such as sodium salts thereof and/or alkyl ester thereof. Preferably, said organic acid is a carboxylic acid selected from the group consisting of lactic acid, malic acid, tartaric acid, citric acid, formic acid, acetic acid, propionic acid, isopropionic acid, oxalic acid, glutaric acid, adipic acid and glycolic acid. More preferably, said organic acid is a carboxylic acid selected from the group consisting of lactic acid, malic acid, citric acid, acetic acid, propionic acid, oxalic acid and adipic acid. Most preferably, said organic acid has a molecular weight lower than 100 g/mol, more preferably lower than 90 g/mol, or even lower than 80 g/mol or 70 g/mol. Preferably, said organic acid is acetic acid or lactic acid, and most preferably acetic acid. It was surprisingly found that such organic acids also act as a viscosity reducing agent. This is advantageous since no further stabilizing agents, such as i.e. magnesium aluminium silicate and/or anionic colloidal silver particles, are mandatory, even at higher contents of the film-forming polymer. Preferably, said organic acid is comprised in an amount of at most 25 wt. %, preferably in an amount of at most 10 wt. %, and more preferably in an amount between 1 wt. % and 5 wt. %. Most preferably, said organic acid is comprised in an amount of 1 wt. %, 2 wt. %, 3 wt. %, 4 wt. % or 5 wt. %, or any amount there in between. Even more preferably, said liquid composition further comprises an acidifying agent such as dehydroacetic acid in an amount of 0.20 wt. %, 0.40 wt. %, 0.60 wt. %, 0.80 wt. % or 1.00 wt. %, or any amount there in between.

In a preferred embodiment, the present invention provides a liquid composition according to the first aspect of the invention, further comprising a nail nutrition and/or nail repair agent such as i.e. biotin, lysine, cysteine, gelatin, pantothenyl alcohol, panthenol and inorganic or organic calcium, magnesium or zinc compounds, acetylated lanolin alcohol derivative, L-proline, . . . Other nail nutrition and/or nail repair agent are known to the person skilled in the art. Preferably, said nail nutrition and/or nail repair agent is comprised in an amount of between 0.01 and 2.50 wt. %. This further enhances the recovery of the treated nail. The person skilled in the art knows the effective amounts of such nail nutrition and/or nail repair agents. Preferably, the liquid composition of the invention comprises one or more adjuvants selected from the group consisting of terpenes or terpene-containing oils, alcohols, ketones, fatty acid esters, polyethylene glycols, surfactants, urea, antioxidants and complexing agents.

In a preferred embodiment, the present invention provides a liquid composition according to the first aspect of the invention, wherein said liquid composition comprises a polishing agent. This allows to render i.e. a nail lacquer smooth and aesthetically attractive. As used herein, the term "polishing agent" is intended to mean a compound used to impart an attractive sheen to solid dosage forms. Such compounds include, by way of example and without limitation, carnauba wax, white wax and other materials known to one of ordinary skill in the art.

In a preferred embodiment, the present invention provides a liquid composition according to the first aspect of the invention, wherein said liquid composition comprises a stabilizing agent. As used herein, the term "stabilizer" or "stabilizing agent" is intended to mean a compound used to stabilize the pharmaceutically active agent against physical, chemical, or biochemical process which would reduce the therapeutic or prophylactic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and other known to those of ordinary skill in the art. Octyl gallate is a known anti-oxidant suitable for use in the present invention. Preferably, said stabilizer is used in an amount of at least 1.00 wt. %, and more preferably in an amount of between 1.00 wt. % and 5.00 wt. %. Most preferably, said stabilizer is used in an amount of between 2.00 wt. % and 3.00 wt. %, such as i.e. 2.5 wt. %.

In a preferred embodiment, the present invention provides a liquid composition according to the first aspect of the invention, wherein said liquid composition comprises one or more preservatives and/or preservative boosters. Preferably, said preservative is used in an amount of at least 0.50 wt. %, and more preferably in an amount of 0.60 wt. %, 0.80 wt. %, 1.00 wt. %, 1.20 wt. % or 1.40 wt. %, or any amount there in between. Suitable preservatives such as 2-phenoxyethanol and iodopropynyl butylcarbamate are known to the person skilled in the art. Preferably, said preservative booster is used in an amount of at least 0.50 wt. %, and more preferably in an amount of 0.60 wt. %, 0.80 wt. %, 1.00 wt. %, 1.20 wt. % or 1.40 wt. %, or any amount there in between. Suitable preservative boosters such as a synergistic blend of 1,2-hexanediol and caprylyl glycol, are known to the person skilled in the art.

The liquid composition of the invention can also include oils, for example, fixed oils, such as peppermint oil, peanut oil, sesame oil, cottonseed oil, corn oil and olive oil; fatty acids, such as oleic acid, stearic acid and isostearic acid; and fatty acid esters, such as ethyl oleate, isopropyl myristate, fatty acid glycerides and acetylated fatty acid glycerides. It can also include alcohols, such as ethanol, isopropanol, hexadecyl alcohol, glycerol and propylene glycol; glycerol ketals, such as 2,2-dimethyl-1, 3-dioxolane-4-methanol; ethers, such as polyethylene glycol-450; petroleum hydrocarbons, such as mineral oil and petrolatum; or mixtures thereof.

In a second aspect, the present invention provides a liquid composition according to the first aspect of the invention for use as a medicament.

In a third aspect, the present invention provides a liquid composition according to the first aspect of the invention for use in treatment of nail diseases and/or infections.

The invention relates to the use as mentioned the novel liquid composition according to the first aspect of the invention for the treatment, prevention, prophylaxis or supportive treatment of nail diseases and periungual diseases as well as for nail care. In particular, the invention relates to the liquid composition according to the first aspect of the invention for the treatment or prevention of fungal infections, such as by *Candida albicans* or *Trichophyton mentagrophytes* infested fingernails or toenails. Furthermore, the novel compositions can also be used to treat fungal infections of hooves, paws and claws of animals. Typical liquid composition according to the first aspect of the invention are useful as antifungal agents, for example, for (i) treatment, prevention and treatment of onychomycosis caused by dermatophytes, yeasts or molds; (ii) mixed infections; (iii) treatment, prevention and treatment of fungal nail infections in patients with psoriasis, diabetes or AIDS; and (iv) support the trreatment of periungual nail infections such as *B. Candida paronychium, Candida albicans* or *Trychophyton mentagrophytes.*

In some embodiments, a composition of the present invention may comprise at least one antibacterial, antiviral and/or antifungal agent. The terms "antibacterial agent", "antiviral agent" and "antifungal agent" are used to refer to an agent known to treat infections with bacteria, viruses and fungi, respectively.

The term "bacteria," as used herein, includes any organism from the prokaryotic kingdom, including gram positive and gram negative bacteria. These organisms include genera such as, but not limited to, *Agrobacterium, Anaerobacter, Aqualbacterium, Azorhizobium, Bacillus, Bradyrhizobium, Cryobacterium, Escherichia, Enterococcus, HeMobacterium, Klebsiella, Lactobacillus, Methanococcus, Methanothermobacter, Micrococcus, Mycobacterium, Oceanomonas, Pseudomonas, Rhizobium, Staphylococcus, Streptococcus, Streptomyces, Thermusaquaticus, Thermaerobacter, Thermobacillus,* and the like.

The term "virus," as used herein, includes any virus, including double-stranded DNA viruses (e.g., adenoviruses, herpes viruses, poxviruses), single-stranded (+)sense DNA viruses (e.g., parvoviruses), double stranded RNA viruses (e.g., reo viruses), single-stranded (+)sense RNA viruses (e.g., picornaviruses, togaviruses), single-stranded (−)sense RNA viruses (e.g., orthomyxoviruses, rhabdoviruses), single stranded (+)sense RNA having a DNA intermediate in the life-cycle (e.g., retroviruses), and double stranded DNA with RNA intermediate (e.g., hepadnaviruses). Exemplary viruses include humanpapilloma virus, herpes simplex virus and poxvirus.

The term "fungus," as used herein, includes any fungus or mold, including arbuscular mycorrhiza, conidiophores, chytridiomycota, blastocladiomycota, neocallimastigomycota, zygomycota and glomeromycota. The term also includes slime molds and water molds. Exemplary fungi include Candida, malassezia furfur, Pityrisporum ovalae, and dermophytes such as Trichophyton, Microsporum and Epidermophyton.

Exemplary nail disorders that may be treated and/or prevented using a composition and/or method described herein include, but are not limited to, nail psoriasis, psoriatic nail dystrophy, onychia, onychiagryposis, onychia trophia, onychocryptosis, onychodystrophy, onychomycosis, onychogriposis, onycholysis, onychomadesis, onychauxis, onychorrhexis, onychoschizia, tinea unguium, onychophosis, onychoptosis, paronychia, pseudomonas, pterygium and pterygium inversum unguis, koilonychia, subungual hematoma or other trauma to the nail, folic acid deficiency, subungual hyperkeratosis, leukonychia, nail patella syndrome, melanonychia, protein deficiency, brittle and peeling nails, methyl methacrylate damaged nails, vitamin C deficiency, vitamin deficiency, tinea unguis, thinning nails associated with lichen planus, Raynaud's disease, nail dystrophy associated with rheumatoid arthritis, beau's lines, Mee's lines associated with certain kinds of poisoning, discoloration, lamellar splitting, longitudinal grooves and/or ridges, transverse grooves, pitting, soft nails, brittle nail syndrome, any combination thereof.

In certain embodiments, a composition and/or method described herein may be used to treat and/or prevent nail dystrophy (i.e., onychodystrophy) in a nail of a subject. "Nail dystrophy" and "onychodystrophy" as used herein refer to a nail that is poorly formed, misshapen, damaged, and/or discoloured. Nail dystrophy may be caused by an endogenous and/or exogenous factor and/or may be a secondary presentation from complete or partial disruption of the nail matrix, proximal nail fold, nail bed, hyponichium, and/or underlying bony phalanx. In some embodiments, nail dystrophy is not induced and/or caused by onychomycosis. In certain embodiments, one or more signs and/or symptoms of nail dystrophy may be treated and/or prevented according to a composition and/or method of the present invention. In some embodiments, nail splitting and/or nail fragility may be treated and/or prevented according to a composition and/or method of the present invention.

According to some embodiments, the nail disorder may be selected from the group consisting of onycholysis (e.g., distal separation of the nail plate), psoriatic nail, onychorrhexis (e.g., longitudinal grooves and/or ridging of the nail plate), subungual hyperkeratosis (e.g., excessive skin cell growth under nail plate), discoloration, onychoschizia (e.g., peeling of the nail plate surface), lamellar splitting, onychomadesis (e.g., proximal separation of nail plate), brittle nail syndrome, transverse grooves, onychauxis (e.g., nail plate thickening), nail pitting, soft nails, nail dystrophy, nail fragility of intact or damaged nails, and any combination thereof.

In certain embodiments, a composition and/or method of the present invention may treat and/or prevent nail splitting and/or nail fragility. In some embodiments, a composition and/or method of the present invention may prevent direct abrasion and/or friction on a nail surface and/or may provide protection against moisture and/or the effects of moisture. In some embodiments, a composition and/or method of the present invention may protect a nail from a subsequent infection (i.e., reinfection) by a fungal disease.

In some embodiments, the nail disorder, such as, but not limited to, nail dystrophy, may be induced and/or caused by an infectious pathogen, such as bacteria, fungi, viruses, parasites, and/or protozoa. In certain embodiments the nail disorder, such as, but not limited to, nail dystrophy, may be induced and/or caused by a fungus. According to some embodiments, a composition and/or method of the present invention may prevent a nail disorder induced and/or caused by an infectious pathogen.

Also disclosed herein are compositions and/or methods of improving the appearance of a nail compared to the appearance of a nail in the absence of a composition and/or method of the present invention. In some embodiments, a composition and/or method of improving the appearance of a nail of a subject may comprise topically applying a composition described herein to the nail of the subject, thereby improving the appearance of the nail. In certain embodiments, a composition and/or method of the present invention may improve nail growth, colour, surface smoothness, shape, and/or thickness of said nail.

In some embodiments, a composition and/or method of the present invention may improve the appearance of a nail by increasing or improving nail health compared to nail health in the absence of a method of the present invention. Nail health may be evaluated by how the nail grows, the nail colour, the smoothness of the nail, the shape of the nail, and/or the thickness of the nail. For example, the composition and/or method may increase or improve nail health by decreasing yellowing and/or discoloration of a nail; decreasing nail dullness; decreasing nail ridges (e.g., longitudinal and/or horizontal ridges), pits, and/or the like; decreasing nail peeling, splitting, cracking, and/or the like; increasing proper nail growth; decreasing nail thickness; decreasing onycholysis; decreasing subungual hyperkeratosis; increasing nail strength; and any combination thereof.

The present invention finds use in both veterinary and medical applications. Subjects suitable to be treated with a composition and/or method of the invention include, but are not limited to, avian and mammalian subjects. Mammals of the present invention include, but are not limited to, canines, felines, bovines, caprines, equines, ovines, porcines, rodents (e.g. rats and mice), lagomorphs, primates (e.g., simians), non-human primates (e.g., monkeys, baboons, chimpanzees, gorillas), and the like. Any mammalian subject in need of being treated according to the present invention is suitable. Human subjects of both genders and at any stage of development (i.e., neonate, infant, juvenile, adolescent, adult) may be treated according to the present invention. In some embodiments of the present invention, the subject is a mammal and in certain embodiments the subject is a human. Human subjects include both males and females of all ages including neonatal, infant, juvenile, adolescent, adult, and geriatric subjects as well as pregnant subjects. In particular embodiments of the present invention, the subject is a human adolescent and/or adult.

Illustrative avians according to the present invention include chickens, ducks, turkeys, geese, quail, pheasant, ratites (e.g., ostrich) and domesticated birds (e.g., parrots and canaries). The compositions and/or methods of the present invention may also be carried out on animal subjects, particularly mammalian subjects such as mice, rats, dogs, cats, livestock and horses for veterinary purposes and/or for research and development purposes.

In particular embodiments of the present invention, the subject is in need of a composition and/or method of the present invention, e.g., the subject has been diagnosed with, is at risk for, and/or is believed to have a nail disease or disorder that may be treated using a composition and/or method of the present invention. In some embodiments, the subject has a nail disorder, such as, but not limited to, nail dystrophy.

The frequency of application of the inventive liquid composition depends on the degree and the localization of diseases. In general, one single application per day is sufficient. The liquid composition is preferably applied directly to the diseased nail or to the hoof, claw or claw and if necessary also applied to surrounding skin segments using an applicator.

The amount of liquid composition applied is preferably sufficient to form a film with a thickness of at least 0.5 mm and preferably between 0.7 mm and 2.0 mm, and most preferably of about 0.8 mm, 1.0 mm, 1.2 mm, 1.4 mm, 1.6 mm or 1.8 mm or any thickness there in between. A sufficiently thick film and a sufficiently high content of pharmaceutically active agent in the liquid composition according to the invention ensures that an effective amount of pharmaceutically active agent is provided to the infected tissue.

In a fourth aspect, the present invention provides a method for providing a liquid composition according to the first aspect of the invention, comprising the steps of mixing at least a pharmaceutically active compound and an aqueous polymer dispersion.

In a fifth aspect, the present invention provides a container comprising a liquid composition according to the first aspect of the invention.

In a preferred embodiment, the present invention provides a container according to the fifth aspect of the invention, wherein said container is provided with a plug and a brush for applying said liquid composition to a subject. Most preferably, said container is a customary tincture bottle of glass or plastic with built-in shutter brush. This allows the user or an administrator to apply the liquid composition according to the invention.

EXAMPLES

In the following examples are intended to further clarify the present invention, and are nowhere intended to limit the scope of the present invention.

Example 1

The current embodiment provides a liquid composition or paste which can be applied on skins or nails of a patient, which paste composition then solidifies to provide a release layer comprising an antimycotic agent to be released in the skin or nail. After one day, the dried composition can easily be removed as a peel-off layer.

A peel-off nail lacquer composition with anti-mycotic activity is presented below. The lacquer is predominantly comprised of an aliphatic poly (urea-urethane) polymer dispersion, further comprising water as a viscosity modifier and an antimycotic agent, acetic acid. A complete list of ingredients and their amounts is provided in Table 1.

The poly (urea-urethane) polymer dispersion is a 50 wt. % polymer dispersion comprising polyurethane-A as a poly (urea-urethane) polymer. Polyurethane-A is a copolymer of 1,4-butanediol, ethylene diamine, hexamethylene diisocyanate, isophorone diisocyanate, and sodium N-(2-aminoethyl)-3-aminoethane sulfonate monomers. The 50 wt. % polyurethane-A dispersion is a colloidal system of a high molecular weight (>50.000 Dalton) poly (urea-urethane) polymer dispersed in water. An internal emulsifier is incorporated into the polymer backbone to ensure stability of the dispersion. Therefore, the use of external surfactants is not required. This polymer was found to perform exceptionally well as a film former in nail lacquer applications according to the invention. The film is very strong and adhesive, but also elastic. These properties allow combination of strong nail adhesion and easy removal. In addition, the occlusive film will enhance hydration of the nail, which in turn stimulates diffusion of acetic acid (polar substance) through the nail. Furthermore, it causes no irritation or redness on the surrounding skin.

The composition showed to be a good-flowing, smooth, homogeneous phase. Upon application of a 1-2 mm thick film to a subject, the film dried within a period of 3 to 4 minutes.

TABLE 1

Nail lacquer composition according to the invention.

| ingredient | content (wt. %) |
| --- | --- |
| acetic acid | 3.00 |
| peppermint oil | 3.00 |
| octyl gallate | 0.50 |
| sorbitan sesquioleate | 1.00 |
| phenethyl alcohol and ethyl hexyl glycerin | 0.50 |
| 1,2-hexanediol & caprylyl glycol | 1.00 |
| dehydroacetic acid and benzyl alcohol | 1.10 |
| polysorbate 80, cetyl acetate, acetylated lanolin alcohols | 0.50 |
| iodopropinyl butylcarbamate (0.01%) | 0.15 |
| biotin | 0.01 |
| water | 9.24 |
| poly (urea-urethane) polymer dispersion | 80.00 |

Acetic acid, CH3COOH, also known as ethanoic acid acts as acidifying agent. Its small size and its hydrophilic properties enables it to penetrate the nail quickly and lower the pH efficiently. Furthermore, its low molecular weight means there are more acid molecules per weight unit, meaning it will take more alkaline substance to neutralize it than larger acids (such as propionic acid or lactic acid). This enables the acid to keep the pH low for a longer period of time, when taking into account the same compensatory production or liberation of alkaline products. This small acid penetrates the nail and lowers the pH of the nail plate, thus preventing fungal development. Although dermatophytes are not necessarily alkaliphilic, they cannot grow under continuous acidic conditions.

Peppermint oil is added as fragrance and solvent for different ingredients. Second to this, the inventors have found that penetration capacity is enhanced by inclusion of peppermint oil. Furthermore, it masks the odour of the included organic acids.

A synergistic blend of 1,2-hexanediol and 1,2-octanediol has different functions: conditioning, emollient, humectant, solvent and preservative booster.

Polysorbate 80, cetyl acetate, acetylated lanolin alcohols is a solubilized acetylated lanolin alcohol derivative in a concentration of 0.5 to 5.0%. It is a mixture of polysorbate 80, cetyl acetate, stearyl acetate, oleyl acetate and acetylated lanolin alcohol. It is a surface active agent and stabilizes the formulation. It is also a superfatting agent to help to prevent dryness of the skin surrounding the nail.

Octyl gallate is the ester of 1-octanol and gallic acid which has an antioxidant activity. The anti-oxidative effect of octyl gallate is important to maintain the characteristics of the peppermint oil and other oxidation-sensitive ingredients by inhibiting oxidative degradation. This allows optimal preservation of the oil-dissolved ingredients and to maintain fragrance properties of the oil.

Dehydroacetic acid or 3-acetyl-6-methyl-2H-pyran-2,4-(3H)-dione (DHA) is added as a preservative and a plasticizer. The addition to the composition allows to form a strong but peelable poly (urea-urethane) polymer film, with strong adhesion to the nail.

Benzoic acid serves as bacteriostatic preservative. During use, the water-based formula is continuously exposed to fungi (and bacteria), present on the human nail.

Indeed, the product is daily applied using a brush for a long time, as curing period can take more than one year, depending on the initial status of the nail infection. The high concentration of water in the formula is an ideal environment to promote microbial growth, which can strongly affect product's efficacy, or even worse, negatively impact nail condition. For these reasons, the product must be properly preserved. Benzoic acid is present in the composition to inhibit bacterial growth therein.

Iodopropynyl butylcarbamate (IPBC) is used as a preservative. Although DHA is already included in the formulation to prevent fungal contamination, IPBC is included to increase the preservative potency of the formulation. It is known that some surfactants may have an impact on the preservative effects of DHA. In order to circumvent this, IPBC was added.

Phenethyl alcohol is an antimicrobial preservative, which is active at pH 6 or lower.

Ethyl hexyl glycerin is combined with a synergistic blend of 1,2-hexanediol and caprylyl glycol, DHA, benzoic acid, and IPBC. Ethyl hexyl glycerin is added in combination with phenethyl alcohol. It boosts the preservative of the latter but also has tissue conditioning properties. Activity of DHA and phenethyl alcohol can be affected by the presence of non-ionic detergents. For this reason, the combination of preservatives allows optimal preservation of the paste composition, as the product is daily prone to bacterial and fungal contamination.

Biotin, also known as vitamin B7, vitamin H or coenzyme R is necessary for cell growth, the production of fatty acids, isoleucine and valine. It also plays a role in gluconeogenesis. Biotin assists in various metabolic reactions involving the transfer of carbon dioxide. As the nails that are suffering from onychomychosis are very brittle and dull, biotin helps to reestablish the growth of a healthy nail by supporting the cell metabolism. This allows the nail to cure faster and to be less prone to reinfection.

Example 2

The current embodiment provides a liquid nail composition according to the invention. Table 2 provides a description of the ingredients of the composition according to Example 2.

The polyurethane-B dispersion is a 41 wt. % polymer dispersion comprising polyurethane-B as a poly (urea-urethane) polymer. Polyurethane-B is a copolymer of copolymer of adipic acid, dicyclohexylmethane diisocyanate, ethylenediamine, hexanediol, neopentyl glycol and sodium N-(2-aminoethyl)-3-aminoethanesulfonate monomers. The polyurethane-B dispersion is a colloidal system of a high molecular weight polyurethane polymer dispersed in water. This polymer functions as a universal film former for high and low viscosity. It can be incorporated into oil-in-water and water-in-oil emulsions as well as in multiple emulsions, gels and gel creams. The polymer structure contains both hydrophilic and hydrophobic segments, which impart a unique combination of water resistance and ease of removal from skin. The polyurethane-B dispersion imparts non-transfer resistant properties to decorative cosmetics. Also, its film creates a natural soft feel.

TABLE 2

Nail lacquer composition according to Example 2.

| ingredient | content (wt. %) |
|---|---|
| acetic acid | 3.00 |
| eucalyptus oil | 2.00 |
| octyl gallate | 3.00 |
| synergistic blend of 1,2-hexanediol and caprylyl glycol | 0.50 |
| dehydroacetic acid | 0.60 |
| TWEEN ® 80 | 1.00 |
| iodopropynyl butylcarbamate | 0.15 |
| ethanol | 6.00 |
| polyurethane-A dispersion, 50 wt. % | 41.87 |
| polyurethane-B dispersion, 41 wt. % | 41.87 |

TWEEN ® 80 is a POE (20) sorbitan monooleate, Polyethylene glycol sorbitan monooleate, Polyoxyethylenesorbitan monooleate, Polysorbate 80, and can be identified by CAS number 9005-65-6.

The composition according to Table 2 showed to provide a smooth, homogeneous, viscous, while liquid. The film obtained upon drying of the liquid on the treated nail showed to have good scratch resistance and could be peeled off as one layer.

Example 3

The current embodiment provides a liquid nail composition according to the invention. Table 3 provides a description of the ingredients of the composition according to Example 3.

TABLE 3

Nail lacquer composition according to Example 3.

| ingredient | content (wt. %) |
|---|---|
| acetic acid | 3.00 |
| eucalyptus oil | 2.00 |
| octyl gallate | 3.00 |
| synergistic blend of 1,2-hexanediol and caprylyl glycol | 0.50 |
| dehydroacetic acid | 0.60 |
| TWEEN ® 80 | 1.00 |
| iodopropynyl butylcarbamate | 0.15 |
| 2-phenoxyethanol | 1.00 |
| ethanol | 5.00 |
| polyurethane-A dispersion, 50 wt. % | 41.87 |
| polyurethane-B dispersion, 41 wt. % | 41.87 |

The composition according to Table 3 showed to provide a smooth, homogeneous, viscous, white liquid. The film obtained upon drying of the liquid on the treated nail showed to have good scratch resistance and could be peeled off as one layer.

Example 4

The current embodiment provides a liquid nail composition according to the invention. Table 4 provides a description of the ingredients of the composition according to Example 4.

TABLE 4

Nail lacquer composition according to Example 4.

| ingredient | content (wt. %) |
|---|---|
| acetic acid | 3.00 |
| eucalyptus oil | 2.00 |
| octyl gallate | 1.33 |
| synergistic blend of 1,2-hexanediol and caprylyl glycol | 1.00 |
| dehydroacetic acid | 0.60 |
| TWEEN ® 80 | 0.67 |
| xantham gum | 0.50 |
| iodopropynyl butylcarbamate | 0.15 |
| 2-phenoxyethanol | 1.00 |
| water | 9.75 |
| polyurethane-A dispersion, 50 wt. % | 80.00 |

The composition according to Table 4 showed to provide a homogeneous, highly viscous, white liquid.

Example 5

The current embodiment provides a liquid nail composition according to the invention. Table 5 provides a description of the ingredients of the composition according to Example 5.

TABLE 5

Nail lacquer composition according to Example 5.

| ingredient | content (wt. %) |
|---|---|
| acetic acid | 3.00 |
| eucalyptus oil | 2.00 |
| octyl gallate | 1.33 |
| synergistic blend of 1,2-hexanediol and caprylyl glycol | 1.00 |
| dehydroacetic acid | 0.60 |
| TWEEN ® 80 | 0.67 |
| xantham gum | 0.50 |
| iodopropynyl butylcarbamate | 0.15 |
| 2-phenoxyethanol | 1.00 |
| water | 9.75 |
| polyurethane-B dispersion, 41 wt. % | 80.00 |

The composition according to Table 5 showed to provide a homogeneous, highly viscous, white liquid.

Comparative Example 6

The current embodiment provides a liquid nail composition according to the state of the art. Table 6 provides a description of the ingredients of the composition according to Example 6.

TABLE 6

Nail lacquer composition according to Comparative Example 6.

| ingredient | content (wt. %) |
|---|---|
| acetic acid | 3.00 |
| decylene glycol | 2.00 |

TABLE 6-continued

Nail lacquer composition according to Comparative Example 6.

| ingredient | content (wt. %) |
|---|---|
| octyl gallate | 3.00 |
| dehydroacetic acid | 0.60 |
| iodopropynyl butylcarbamate | 0.30 |
| 2-phenoxyethanol | 1.00 |
| ethanol | 45.00 |
| polyurethane-A dispersion, 50 wt. % | 45.10 |

The composition according to Table 6 showed a thick, cloudy, not-incorporated, heterogeneous solid in a liquid phase. The composition proved not applicable as a nail lacquer or as a nail lacquer for treatment of nail diseases.

What is claimed is:

1. A liquid nail lacquer composition comprising an aqueous poly (urea-urethane) polymer dispersion for providing a film on a nail of a subject in need thereof, wherein said liquid composition comprises said poly (urea-urethane) polymer as film forming polymer, wherein said poly(urea-urethane) polymer is an aliphatic poly(urea-urethane) polymer or a polyether polyurethane polymer, whereby said film forming polymer is comprised in said liquid nail lacquer composition in an amount of at least 25 wt.%, relative to the total weight of the composition, as determined according to DIN EN ISO 3251, and further comprising an organic acid selected from the group consisting of: lactic acid, malic acid, tartaric acid, citric acid, formic acid, acetic acid, propionic acid, isopropionic acid, oxalic acid, glutaric acid, adipic acid and glycolic acid, in amount of at most 10 wt.%.

2. The liquid composition according to claim 1, having a pH of between 2.5 and 6.5, as determined according to DIN ISO 976.

3. The liquid composition according to claim 1, wherein said liquid nail lacquer composition is free of magnesium silicate.

4. The liquid composition according to claim 1, wherein said liquid composition has a viscosity between 250 and 50,000 mPa.s, as determined by DIN EN ISO 3219.

5. The liquid composition according to claim 1, wherein said film has an elongation at break of at least 100%.

6. The liquid composition according to claim 1, wherein said film has a tensile strength at break of at least 5 MPa.

7. The liquid composition according to claim 1, wherein said organic acid is selected of the group consisting of: lactic acid, malic acid, citric acid, acetic acid, propionic acid, oxalic acid and adipic acid.

8. A method of making the liquid composition according to claim 1, comprising the steps of mixing at least said organic acid selected from the group consisting of: lactic acid, malic acid, tartaric acid, citric acid, formic acid, acetic acid, propionic acid, isopropionic acid, oxalic acid, glutaric acid, adipic acid and glycolic acid, and said aqueous poly (urea-urethane) polymer dispersion.

9. A container comprising a liquid composition according to claim 1.

10. The container according to claim 9, wherein said container is provided with a plug and a brush for applying said liquid composition to a subject.

11. The liquid composition according to claim 7, wherein said organic acid is selected from the group consisting of lactic acid and acetic acid.

12. The liquid composition according to claim 7, wherein said organic acid is acetic acid.

13. The liquid composition according to claim 1, wherein said organic acid is used in amount between 1 wt.% and 5 wt.%.

* * * * *